United States Patent [19]

Gradeff et al.

[11] Patent Number: 5,099,006

[45] Date of Patent: Mar. 24, 1992

[54] ALKOXY-TYPE DERIVATIVE COMPOUNDS AND PROCESS FOR PREPARING ALKOXY-TYPE DERIVATIVES OF TRIVALENT GROUP 3B METALS

[75] Inventors: Peter S. Gradeff, Pottersville; Heiko Mauermann; Kenan Yunlu, both of New Brunswick; Carlos M. Ramirez, Piscataway, all of N.J.

[73] Assignee: Rhone-Poulenc Inc., Princeton, N.J.

[21] Appl. No.: 280,541

[22] Filed: Dec. 8, 1988

Related U.S. Application Data

[63] Continuation-in-part of Ser. No. 144,326, Jan. 14, 1988, abandoned.

[51] Int. Cl.$^5$ .................. C07F 5/00; C01F 17/00
[52] U.S. Cl. ........................................ 534/15; 423/263
[58] Field of Search ..................... 534/15; 423/263

[56] References Cited

U.S. PATENT DOCUMENTS

| Re. 8,938 | 8/1976 | Koda et al. | 260/448.2 |
|---|---|---|---|
| 3,884,950 | 5/1975 | Koda et al. | 260/492.2 |
| 4,070,343 | 1/1978 | Kishimoto et al. | 260/45.75 F |
| 4,489,000 | 12/1984 | Gradeff et al. | 260/492.2 |
| 4,492,655 | 1/1985 | Gradeff et al. | 260/492.2 |
| 4,663,439 | 5/1987 | Gradeff et al. | 534/15 |
| 4,800,072 | 1/1989 | Gradeff et al. | 423/396 |
| 4,801,692 | 1/1989 | Gradeff et al. | 534/15 |

FOREIGN PATENT DOCUMENTS

| 2362954 | 6/1974 | Fed. Rep. of Germany. |
| 2554498 | 6/1976 | Fed. Rep. of Germany. |
| 1424481 | 1/1966 | France. |
| 2213316 | 8/1974 | France. |
| 2505356 | 11/1982 | France. |
| 41046 | 4/1976 | Japan. |
| 32563 | 3/1979 | Japan. |
| 146897 | 11/1979 | Japan. |
| 58253 | 4/1980 | Japan. |

OTHER PUBLICATIONS

Batwara et al., Synthesis of Silyoxides of Gad Linium and Erbium, J. Inerg. Nucl. Chem., vol. 32, 411–415 (1970).

Reactions of Carbon Dioxide with Bis (Trimethylsilyl) Amino Derivatives of Lanthanides, J. of Gen. Chem. of U.S.S.R., p. 336 (1986).

A Novel Synthesis of Thea-Hydroxy Ketone Moiety of Anthracyclinones by the Use of 2-Trimethyl-Silyl--Ethyl Cerium III Reagents, Suzuki et al., 18 Technocrat, p. 102 (Jan. 1985).

Increase in the Thermal and Oxidative Stability of Some Halogen-Containing Poly (Organosiloxanes) by Iron, Cerium and Copper Compounds, Zubkova et al., Zh, Khim 1979 (Abstract 1, p. 303).

*Primary Examiner*—Robert L. Stoll
*Assistant Examiner*—C. Harris
*Attorney, Agent, or Firm*—Morgan & Finnegan

[57] ABSTRACT

Alkoxy-type derivative compounds are a process for preparing alkoxy-type derivatives of trivalent Group 3b metals, e.g., cerium (III), such as alkoxides, siloxides or alkanolatoamines from an anhydrous complex of trivalent Group 3b metals, e.g. cerium ammonium nitrate complex, in the presence of an alcohol, silanol or alkanolamine and a base or by employing the complex and alkali salts of the alcohol, silanol, or alkanolamine.

53 Claims, No Drawings

ALKOXY-TYPE DERIVATIVE COMPOUNDS AND PROCESS FOR PREPARING ALKOXY-TYPE DERIVATIVES OF TRIVALENT GROUP 3B METALS

CROSS-REFERENCE TO RELATED APPLICATION

This application is a continuation-in-part application of Ser. No. 07/144,326, filed Jan. 14, 1988, incorporated herein by reference, abandoned.

BACKGROUND OF THE INVENTION

1. Field of the Invention

This invention pertains to alkoxy-type derivatives of Group 3b metals including trivalent rare earth metals, exemplified by cerium, such as alkoxides, silyloxides, or alkanolatoamine compounds, and methods for preparing these compounds. 2. Discussion of Background Polyvalent metal alkoxy derivatives are versatile organometallic compounds. The alkoxides, for instance, have been used as paint additives, water repellents, adhesion promoters, mordants, sizing agents in enamel compositions, catalysts, precursors for ceramics and fibers and also as intermediates in the synthesis of other metal-organic compounds. There are four general preparative methods for metal alkoxides all under anhydrous conditions, as follows:

A. By reaction of the corresponding alcohol and metal, such as the alkali metals, alkaline earth metals, and aluminum, with the assistance of an alkaline earth or acidic catalyst.

B. By reaction of the corresponding alcohol with the oxides and hydroxides of the metal, for instance NaOH or $Na_2O$, $V_2O_5$ and $MoO_3.2H_2O$.

C. By reaction of the corresponding alcohol and metal halide in the presence of an anhydrous base. A typical example is the preparation of $Th(OR)_4$ or $Zr(OR)_4$:

$$ThCl_4 + 4ROH + 4NaOR \rightarrow Th(OR)_4 + 4NaCl$$

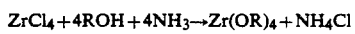

$$ZrCl_4 + 4ROH + 4NH_3 \rightarrow Zr(OR)_4 + NH_4Cl$$

The reaction can be used for preparing alkoxides of titanium, hafnium, germanium, niobium, tantalum, aluminum and tin.

D. By transetherification of the metal alkoxides of lower alcohols, such as the methoxides, ethoxides or isopropoxides, with a higher alcohol.

Method A is exemplified for a number of yttrium, lanthanum and other lanthanide alkoxides by L. Brown and K. Mazdiyasni in *Organic Chemistry*, (1970) p. 2783. The reaction, previously thought to be useful only for the alkali metals magnesium and aluminum, was extended by them to the synthesis of yttrium and all of the lanthanide isopropoxides. For the lower lanthanides, such as lanthanum, cerium, praesodymium and neodymium, a mixture of $HgCl_2$, and $Hg(C_2H_3O_2)_2$ or $HgCl_2$ is used as a catalyst, to increase both the rate of reaction and percent yield Generally, 5 g of the metal turnings is reacted with about 300 ml of isopropyl alcohol at reflux temperature for about 24 hours and in the presence of a small amount of Hg salt catalyst. The yields are said to be 75% or better.

Most of the other examples in the literature of the preparation of alkoxides of lanthanides refer to the use of corresponding metal halides. In some cases, a complex $LaCl_3.3ROH$ is preferred to the $LaCl_3$ (Misra et al., *Austr. J. Chem.* 21 p. 797 (1978) and Mehrotra and Batwara, *Inorganic Chem.* 9 p. 2505 (1970).

An interesting variation of Method D is mentioned by Tripathi, Batwara and Mehrotra, *J.C.S.A.* (1976) p. 991. Lower ytterbium alkoxides (such as methoxide and ethoxide) were synthesized from ytterbium isopropoxide, by transetherification with methanol or ethanol. Owing to their sparing solubility, these alcohols were removed by precipitation as the reaction proceeded, driving the transetherification to completion.

In general, Methods A, B and C are only suited for preparation of the lower alkoxides, such as the methoxides, ethoxides and isopropoxides, since the reactivity of higher alcohols diminishes with increase in their molecular weights. The higher alkoxides are better prepared by Method D, which is a two-step process.

U.S. Pat. Nos. 4,489,000 and 4,492,655 to Gradeff and Schreiber describe the preparation of tetravalent cerium alkoxides from ceric ammonium nitrate and are incorporated by reference. U.S. Ser. No. 895,560 relates to tetravalent alkanolatoamine derivatives and method for preparation from ceric ammonium nitrate and is incorporated by reference. U.S. Pat. No. 4,663,439 to Gradeff and Schreiber disclose a process for preparing ceric alkoxides and is incorporated by reference.

Modern separation techniques for lanthanides yield these elements primarily as chlorides or nitrates in aqueous solution. They are used to make all other derivatives such as carbonates, hydroxides, oxides, etc. They can also be used to make some of the organic derivatives, such as high alkyl carboxylates or acetyl acetonates. Anhydrous lanthanide inorganic salts, however, are essential for making alkoxides, Ln-carbon bond derivatives and a host of others, as well as for the production of metals by electrolytic and metallothermic processes. Oxides can be made anhydrous, but their low solubility and limited reactivity precludes their use in many areas. The halides are the only class of compounds that are being used as a source of anhydrous species suitable for these purposes. The easiest ones to make are the fluorides, but they have only limited use in syntheses due to extremely low solubility and reactivity. Among the most difficult ones to dehydrate are the iodides. The bromides and chlorides present a similar degree of difficulty which is greater than the fluorides but less than the iodides. In view of economic and environmental considerations, the chlorides are the most sought anhydrous lanthanide salts. This includes cerium, the most abundant among the lanthanides.

The halides which separate from their aqueous solutions, usually retain 6-7 moles of water. After the unbound water has been removed, most of the bound water can be removed by careful dehydration below 100° C. It is extremely difficult, however, to remove the last mole of water without decomposing the halide.

Dehydration of lanthanon chloride hydrates done with HCl gas is a tedious process. Dehydration using ammonium chloride in addition to HCl, and at temperatures below about 200°-300° has shown better results. Oxides have been reacted with sulfur monochloride and chlorine or sulfur monochloride alone. Thionyl chloride, carbon tetrachloride and phosgene have also been used as reagents. Preparation of the most commonly used anhydrous salt of lanthanides, the chloride, is not an easy task. (*Chem. Rev.*, 1962, pp. 503-511).

U.S. Pat. No. 4,492,655 to Gradeff and Schreiber discloses the preparation of Cerium(III) cyclopentadienyl derivatives using Ceric Ammonium Nitrate and Na-cyclopentadienyl. Use of a nitrate represented a departure from conventional routes. Ceric ammonium nitrate was advantageous in that it was easily obtained in anhydrous form. The process of that invention comprises slowly adding alkali metal cyclopentadienide to a solution of ceric ammonium nitrate, and forming in sequence mono- to tricyclopentadienyl cerium. The overall reaction equation is shown as $$2[Ce(NO_3)_4 \cdot 2NH_4NO_3] + 12NaCp \rightarrow 2Ce(Cp)_3 + 4CpH + (Cp)_2 + 12NaNO_3 + 4NH_3.$$

The "in situ" reduction step is shown to proceed via two possible pathways.

$$Ce(NO_3)_4 + 4NaCp \rightarrow [Ce(Cp)_4] + 4NaNO_3$$
$$[2Ce(Cp)_4] \rightarrow [2Ce(Cp)_3] + Cp_2 \quad (a)$$

$$Ce(NO_3)_6 \cdot 2NH_4 + NaCp \rightarrow [Ce^{+4}Cp(NO_3)_5 \cdot 2NH_4] + NaNO_3 \rightarrow Ce^{+3}(NO_3)_5 \cdot 2NH_4 + \tfrac{1}{2}Cp \cdot Cp \quad (b)$$

The above "in situ" reaction has utility in cases where reagent is a good reducing agent whereby part of the reagent is consumed in the reduction of $Ce^{+4}$ to $Ce^{+3}$. In cases as the above referred one, this can be rather expensive.

SUMMARY OF THE INVENTION

It is an object of the present invention to produce an anhydrous complexes of nitrates of trivalent Group 3b metals including yttrium and the lanthanides such as cerium.

It is another object of the present invention to produce alkoxy derivatives of trivalent Group 3b metals including yttrium and the lanthanides such as cerium.

The present invention relates to a convenient process for making anhydrous nitrates and alkoxy derivatives of trivalent Group 3b metals (lanthanons) including yttrium and the lanthanides such as cerium. It uses a new starting material and synthetic path which obviates using the expensive anhydrous trivalent lanthanide halides to produce various alkoxy derivatives, some of which are known and some of which are novel compounds.

In accordance with the invention, anhydrous trivalent Group 3b metal, e.g., lanthanide alkoxy derivatives can be prepared by reacting, under anhydrous conditions, an anhydrous lanthanon nitrate-alkali metal complex or an anhydrous lanthanon nitrate-ammonium nitrate complex with a suitable alcohol, silanol or alkanolamine as defined hereinafter in the presence of a base. These anhydrous derivatives can also be made by reacting the complex with an alkali metal salt of the alcohol, silanol or alkanolamine which corresponds to the in situ intermediate formed when the alcohol, silanol or alkanolamine is in the presence of the aforementioned base. The anhydrous trivalent lanthanon nitrate-alkali or ammonium nitrate complex can be prepared by various procedures as discussed hereinafter.

DETAILED DESCRIPTION OF THE INVENTION

The present invention is directed to the preparation of anhydrous nitrate complex and lanthanon alkoxy derivatives. By lanthanon or lanthanides it is intended to include those trivalent metals of Group 3b of the Periodic Table of Elements (excluding the actinides) including yttrium (atomic No. 37), and the lanthanides of atomic numbers 57-71 and mixtures thereof. Particularly important are the more abundant members such as yttrium, lanthanum, cerium, praesodymium, and neodymium. The most preferred rare earths include yttrium, lanthanum and cerium.

In reference to cerium, these and other objectives can also be accomplished by using previously dried ceric ammonium nitrate, a commercially available Ce(IV) compound. According to one process of the present invention, anhydrous cerous nitrate-ammonium nitrate complex, formed by reacting anhydrous ceric ammonium nitrate (CAN) with a suitable reducing agent under anhydrous conditions is reacted with an alcohol, silanol, or alkanolamine designated as HOX in the presence of a base, and in the absence of water, to produce anhydrous trivalent cerium alkoxy type derivatives.

In one embodiment of the invention (Process A), the anhydrous CAN is treated with ammonia under anhydrous conditions to obtain anhydrous cerous nitrate-ammonium nitrate complex which is then reacted in the absence of water with an alcohol, silanol, or ethanolamine in the presence of a base.

In another embodiment (Process B), dry CAN is contacted with any other suitable reducing agent until completely reduced to $Ce^{+3}$. The resulting $Ce^{+3}$ species is then reacted with the desired alcohol, silanol, or alkanolamine (i.e. ethanolamine) in the presence of a base and in the absence of moisture.

PROCESS A $$3(NH_4)_2Ce(NO_3)_6 + 4NH_3 \rightarrow 3Ce(NO_3)_3 + \tfrac{1}{2}N_2 + 9NH_4NO_3 \quad \text{Eq. A-1}$$

$$Ce(NO_3)_3 + 3HOX + 3NH_3 \rightarrow Ce(OX)_3 + 3NH_4NO_3 \quad \text{A-2}$$

Process A comprises treating dried anhydrous ceric hexanitro ammonium complex (also called ceric ammonium nitrate (CAN)) with ammonia according to Eq. A-1 whereby $Ce^{+4}$ is reduced to $Ce^{+3}$ under anhydrous conditions. The resulting complex of $Ce^{+3}$ nitrate and ammonium nitrate, is used as a source of anhydrous $Ce^{+3}$ salt. Ammonia is economical and yields a simple by-product, nitrogen, in addition to ammonium nitrate.

Ceric ammonium nitrate is a commercial product that can be freed of all water by simple drying in an oven at 105°-120° C., and atmospheric pressure for about 6-12 hours, or under vacuum at lower temperature. According to the present invention, dried CAN, either in solid state or while suspended/dissolved in an appropriate inert solvent, is contacted with ammonia gas.

Efforts to isolate $Ce(NO_3)_3$ in a free state did not succeed. Apparently, $Ce^{+3}$ ion needs to be additionally coordinated. Ammonium nitrate helps achieve this coordination and allows removal of the water at lower temperatures thus arriving at the anhydrous state. As in the case of CAN and other common examples for lanthanide elements, coordinated ligands can be removed in subsequent reactions if desired and do not present a major problem. A certain amount of $NH_3$ also becomes molecularly bonded to the cerium nitrate complex, and in some instances its presence may be desirable. When for instance, the resulting anhydrous $Ce^{+3}$ product is to be reacted with an alcohol or silanol in the presence of $NH_3$, the coordinated $NH_3$ serves as a portion of the $NH_3$ required. In other cases its presence may not be desirable and steps must be taken to remove it, such as pumping under vacuum, under heating, neutralizing with dry HCl or displacing with another coordinating agent.

Treatment of solid, previously dried CAN with $NH_3$, can be done in a variety of ways. Contact of CAN with $NH_3$ could be maintained for a period of time sufficient to reduce all $Ce^{+4}$ to $Ce^{+3}$. The time necessary to achieve this depends on the mode of contact, granulometry of the CAN, temperature and pressure. Contact of CAN with $NH_3$ can be done at atmospheric pressure while, for instance, stirring the CAN in an atmosphere of $NH_3$. The ammonia can also be maintained under pressure or used as a liquid. When liquid $NH_3$ is used, the excess is easily recovered after the reaction has been completed.

The temperature during contact can be as low as the temperature of liquid ammonia or as high as about 130° C., but below the temperature of decomposition of CAN which starts at about 170° C.

CAN can be reduced while in suspension or in solution in inert solvents such as benzene, pentane, petroleum ethers or glymes. The product need not be isolated from the inert solvent. Once complete reduction with $NH_3$ has been achieved, reagents can be added to accomplish subsequent conversion of the anhydrous $Ce^{+3}$ nitrate complex to the desired new derivative.

The anhydrous cerous nitrate complex, either in solid or in suspension in an inert solvent, is mixed with alcohol, silanol or alkanolamine. A base is then added, such as $NH_3$, alkali metal, or the alkali metal salt of an alcohol, silanol or alkanolamine. The alcohol, silanol or alkanolamine form a corresponding salt in situ by contacting the base. Thus another approach is to mix the complex with the alkali salt corresponding to the alcohol, silanol or alkanolamine. If the alcohol, silanol or alkanolamine is mixed with an alkali salt of the same alcohol, silanol or alkanolamine, then the alcohol acts as a solvent and the reaction proceeds between the complex and the salt. If the alcohol, silanol or alkanolamine is mixed with an alkali salt of a different alcohol, silanol or alkanolamine, there could be exchange of ligands so that ligands from either the alcohol, silanol or alkanolamine, or the salt could react with the complex.

The product is normally kept in solution by using an appropriate inert solvent such as DME, other glymes, tetrahydrofuran (THF), benzene, toluene, etc. The solvent may be filtered off from the ammonium or alkali metal nitrate by-product.

PROCESS B

While reducing CAN with $NH_3$ is the most efficient and inexpensive way to produce the desired $Ce^{+3}$ nitrate complex, a host of other reducing agents are suitable for this invention. Equations B-1 and B-2 illustrate the process:

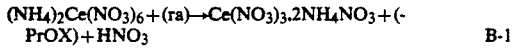

$(NH_4)_2Ce(NO_3)_6 + (ra) \rightarrow Ce(NO_3)_3.2NH_4NO_3 + (PrOX) + HNO_3$  B-1

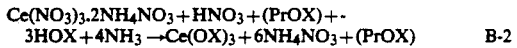

$Ce(NO_3)_3.2NH_4NO_3 + HNO_3 + (PrOX) + 3HOX + 4NH_3 \rightarrow Ce(OX)_3 + 6NH_4NO_3 + (PrOX)$  B-2

(ra) is a reducing agent which can be, for instance, HOX, such as one intended to also provide the alkoxy OX ligand preferably low alkyl alcohol whereby the (PrOX) is less obstructive and easier to remove.

The feature that distinguishes this process from U.S. Pat. No. 4,492,655 is the $Ce^{+4}$ must be reduced to $Ce^{+3}$ prior to reaction. If this essential reduction step does not take place, the resulting products of the overall reaction will be the $Ce^{+4}$ alkoxy derivatives, as described in U.S. Pat. Nos. 4,489,000, 4,492,655 and U.S. Ser. No. 895,560, and not the desired $Ce^{+3}$.

Many reducing agents are suitable for reducing $Ce^{+4}$ to $Ce^{+3}$ according to the invention. One extreme example is dimethoxyethanol (DME), considered an inert solvent. DME reacts with CAN at reflux temperature to totally reduce $Ce^{+4}$ to $Ce^{+3}$. The most useful reducing agents however, because of their low cost, relative ease to accomplish the reaction and relative ease to remove the product of oxidation (PrOX), if necessary, are low alkyl alcohols such as methanol, ethanol, propanol, isopropanol, etc. Generally, the reducing agent suitable for the present invention is one that will react as a reducing agent in anhydrous medium, and lead to substantially complete reduction of $Ce^{+4}$ to $Ce^{+3}$. The reduction may proceed fast or slow depending on the reducing agent. It can be sped up if desired by UV irradiation, heating, or addition of an appropriate catalyst. During this step of the process, the $Ce^{+4}$ is reduced to $Ce^{+3}$ while the medium remains anhydrous. As shown in equation B-1, nitric acid is produced during the reduction and it will remain as such in the mixture if the reducing agent is a neutral species such as alcohol. Besides nitric acid, the mixture will also contain an oxidation (PrOX) by-product. In most cases the nitric acid and the (PrOX) can be kept in for the 2nd step which consists of reacting the desired alcohol, silanol or alkanolamine with the reduced $Ce^{+3}$ in the presence of a base which also will neutralize the acid. However, the nitric acid can be neutralized and the PrOX removed from the system prior to reaction with HOX.

In another embodiment of the invention, anhydrous Group 3b trivalent metal nitrate complexes can be easily prepared by forming the nitrate complexes of Group 3b trivalent metal nitrates under non-anhydrous conditions followed by drying the hydrated complexes under temperatures sufficient to dehydrate but insufficient to substantially (less than 5%) decompose the complexes. The hydrated complexes can be simply prepared by admixing aqueous solutions of trivalent Group 3b metal nitrates with an alkali metal nitrate or ammonium nitrate solution.

By alkali metal it is intended to cover lithium, potassium and, preferably, sodium. The use of the sodium nitrate in forming the complexes provides an advantageous process when using a sodium salt of an organic alkoxy compound in preparing the alkoxy derivatives. The reaction results in the formation of sodium nitrate as a precipitate as shown in the following equation for cerium.

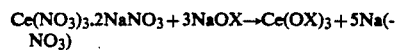

$Ce(NO_3)_3.2NaNO_3 + 3NaOX \rightarrow Ce(OX)_3 + 5Na(NO_3)$

The NaOX may be directly combined with the cerium or other trivalent Group 3b metal complex or may form in situ by combining an alcohol, silanol or alkanolamine with an alkali metal or ammonia in the presence of the metal nitrate complex. The sodium (or other alkali metal) salt of an alcohol, silanol or alkanolamine may be employed as a base for the reaction with the nitrate. However, the initial product may exchange ligands if the reaction is carried out in the presence of another alcohol, silanol or alkanolamine. The sodium nitrate formed as a by-product of the alkoxy reaction can be recycled for use in forming the complexes, thereby avoiding the loss of ammonia which is a by-product formed when using ammonium nitrate.

By Group 3b trivalent metals it is intended to mean scandium, yttrium and the rare earths lanthanum and the lanthanides. The actinides are not considered practical at this time and are excluded. The formation of cerous nitrate by reduction of CAN has been discussed hereinbefore.

The Group 3b trivalent metal nitrate ammonium nitrate complexes can be easily prepared by simple admixture under non-anhydrous conditions. If an aqueous solvent is used, it is preferred to evaporate the solvent prior to drying under vacuum. Various modes of evaporation dryness can be employed.

The dry hydrated complex containing water of crystallization (coordination), can then be dehydrated by heating. Preferably the heating occurs under vacuum to speed the drying. Surprisingly, it has been found that these nitrate complexes can be dehydrated to their anhydrous state at lower temperature and without decomposition: unlike the corresponding halides. Temperatures and times sufficient to remove the desired amount of water without causing substantial decomposition of the nitrate ammonium nitrate complexes can be employed in drying and can be easily determined by one of ordinary skill. Agitation can be employed if desired.

Of course, the evaporation of the solvent and the removal of the water of crystallization can be accomplished in a continuous process as would be readily apparent to one of ordinary skill.

The vacuum used in the preparation of the complexes can range from atmospheric to the lowest vacuum attainable. Vacuums of from 100 mm Hg to 400 mm Hg and lower have been effectively used. Preferably the pressure is less than 300 mm Hg, most preferably less than 100 mm Hg.

Temperatures of a degree sufficient to cause rapid evaporation or dehydration without substantial decomposition of the complex should be used. Temperatures within the range of from about 50° C. to about 160° C. and preferably from about 80° C. to about 130° C. have been found effective.

The ammonium nitrate and/or alkali metal nitrate need to be admixed with the hydrated trivalent Group 3b metal nitrate in an amount sufficient to allow for dehydration to take place at temperatures low enough to prevent substantial decomposition. In practice, sufficient ammonium or alkali metal nitrate is added to displace the water that is strongly coordinated to the metal. The bidendate oxygenated ligand of the added nitrates helps to displace the water which otherwise is difficult to remove. It has been found that molar ratios of Group 3b metal nitrates to ammonia or alkali metal nitrates in the range of 1:1 to 1:5 are used effectively.

The anhydrous trivalent Group 3b metal nitrate ammonium nitrate complexes are hydroscopic. Immediate use and care in handling may be required to maintain the anhydrous condition.

The anhydrous Group 3b metal nitrate complexes find particular use in preparing organic derivatives where an anhydrous starting material is a necessity. The alkoxy derivatives disclosed herein can be made using the Group 3b metal nitrate complexes described above. Other uses can be similarly developed.

The type of alkoxy derivatives that are subject to this invention can be presented as follows:

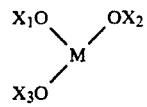

where M is a lanthanon or lanthanide, for example cerium, $OX_1$, $OX_2$ and $OX_3$ are selected from the group consisting of (a) $NO_3$;
(b) OR;
(c) $OSi(R')_y$; and (d) $(OR'')_y N-(R''')_x$.
  |
  $(R''OH)_z$ R is a saturated or unsaturated hydrocarbon, that is aliphatic or aromatic, having 1 to 20 carbon atoms. Preferably R represents a straight, branched or cycloaliphatic hydrocarbon.

R' is the same or different and is a saturated or unsaturated hydrocarbon having 1 to 20 carbon atoms or an alkoxy group having 1 to 10 carbon atoms. The silicon atom is attached to the oxygen atom of the alkoxy group. R' may be a straight, branched, cycloaliphatic, or aromatic hydrocarbon or alkoxy group. Preferably R' has 1 to 10 carbon atoms and is straight, branched or aromatic. Most preferably R' has 1 to 6 carbon atoms, for example, R' may be methyl, ethyl, vinyl or phenyl.

R'' is the same or different and is a hydrocarbon having 1 to 20 carbon atoms. R'' preferably has 1 to 6 carbon atoms. R'' is most preferably ethyl.

R''' is a hydrocarbon having 1 to 20 carbon atoms or a hydrogen atom. R'' preferably has 1 to 6 carbon atoms. R''' is most preferably ethyl, methyl or a hydrogen atom.

R, R', R'' or R''' may be independently substituted or unsubstituted. None, one or two of $OX_1$, $OX_2$ or $OX_3$ are group (a); the remaining three, two or one of $OX_1$, $OX_2$ or $OX_3$ are either of the group (b), (c) or (d); and any two of $X_1$ and $X_2$ and $X_3$ of the same or different molecule of formula I can be taken together as a single group (e), (f) or (g):

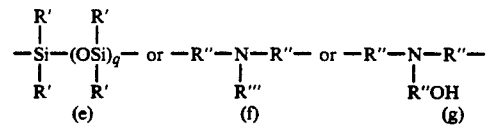

If the molecule of formula I includes $Si(R')_y$, then the number of $Si(R')_y$ groups can be 1, 2 or 3 and y in (c) can be 1, 2 or 3 (preferably 3). When y=2, the silicon of (c) is linked to two of the oxygens as

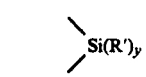

in either (1) the same or (2) a different cerium, or other trivalent Group 3b metal, atom. In (1) the species are monomeric. In (2), they are preferably oligomers or polymers.

Parameter y in (d) can be 1, 2 or 3. Parameter z and parameter x can independently be 0, 1 or 2 and x+y+z is 3. When y is 2 or 3, the linkage is to the same trivalent Group 3b (i.e. cerium) atom, or to different trivalent group 3b (i.e. cerium) atoms (as for example by group (f) or (g)) to form oligomers or, more likely, polymers. Parameter q ranges from zero to about 1000.

When parameter $y=1$ for substituent (c) or $y=3$ for substituent (d), the substituent (c) or (d) links to any 3 of the oxygen atoms of $OX_1$, $OX_2$ and $OX_3$ such that a single substituent substitutes for any three of $X_1$, $X_2$ or $X_3$, respectively. The three oxygen atoms are linked to the same group 3b atom or different group 3b atoms. The single substituent is selected from the following:

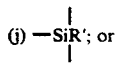

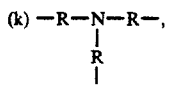

wherein R and R' are defined as above.

Derivatives containing nitro groups (a) are normally obtained when the reactant alcohol, silanol or alkanolamine is added in amounts less than the stoichiometric amounts required to replace all $NO_3$ groups of the trivalent Group 3b metal, e.g., cerous, nitrate.

Exemplary of alcohols supplying OR are methanol, ethanol, propanol, butanol, isobutanol, pentanol, isoheptanol, isopropanol, hexanol, 2-ethyl hexanol, heptanol, isoheptanol, octanol, decanol, benzyl alcohol and other alcohols having from 1 to about 20 carbon atoms. These alcohols may be saturated or unsaturated, straight, branched or cyclic, aromatic or alkyl aromatic.

Exemplary of the silanols that correspond to the $OSi(R')_y$ group are:

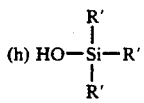

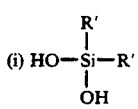

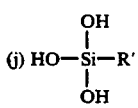

and

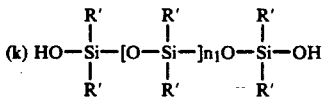

wherein $n_1$ is the number of such units in the polymer and can range from 0 to 1000, preferably 1 to about 10. Group (k) includes solid silicone resins containing OH groups which can be solubilized and used in the reaction with trivalent metals of Group 3b, e.g., cerous, ammonium nitrate to form silicone resin linked to the trivalent metal, e.g., cerous, via the oxygen. R may be hydrogen or the hydrocarbyl group desired in the silyloxide product. The various R' groups attached to a given silicon atom may be either the same or different from each other.

The following structures are examples of silanols suitable for the present invention. (Me represents $CH_3$, Ph represents phenyl).

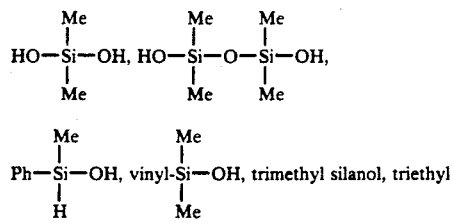

silanol, triphenyl silanol, Ph—Si—Ph,

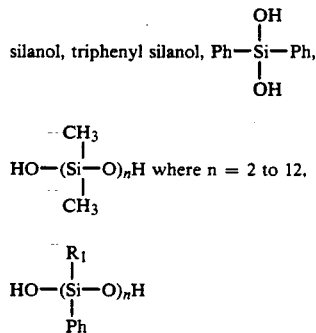

where $n=4$ and $R_1$ = hydrocarbons having 1 to 6 carbon atoms,

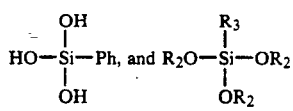

where $R_2$ = methyl, ethyl, propyl, isopropyl or butyl, and $R_3$ = methyl, ethyl, vinyl, or phenyl.

By silanols, the present invention may employ silanols, silanediols or silanetriols having 2 or 3 aliphatic groups of hydrocarbons, some examples of these are as follows: trimethylsilanol, triethylsilanol, tripropylsilanol, triisopropylsilanol, tributylsilanol, triisobutylsilanol, tri-(sec-butyl)silanol, tri-(tert-butyl)silanol, tripentylsilanol, triisopentylsilanol, tri-(sec-pentyl)silanol, tri-(tert-pentyl)silanol; dimethylsilanediol, diethylsilanediol, dipropylsilanediol, diisopropylsilanediol, dibutylsilanediol, diisobutylsilanediol, di-(sec-butyl)-silanediol, di-(tert-butyl)silanediol, di-pentylsilanediol, diisopentylsilanediol, di-(sec-pentyl)silanediol, di-(tert-pentyl)silanediol, methylsilanetriol, ethylsilanetriol, propylsilanetriol, isopropylsilanetriol, butylsilanetriol, isobutylsilanetriol, sec-butyl-silanetriol, tert-butyl-silanetriol, pentylsilanetriol, isopentylsilanetriol, sec-pentyl-silanetriol, tert-pentyl-silanetriol.

The invention may also employ higher aliphatics (6 to 20 carbon atoms), cycloaliphatics or aromatics having 6 to 20 carbon atoms, or mixtures thereof with lower aliphatics. Examples of silanols having higher aliphatics, cycloaliphatics and aromatics either with or without a lower aliphatic ligand are as follows: trihexylsilanol, triheptylsilanol, triisoheptylsilanol, trioctylsilanol, triisooctylsilanol, tri-(ethyl-2-hexyl)-silanol, tri-(sec-octyl)-silanol, tri-(tert-octyl)-silanol, trinonylsilanol, triisononylsilanol, tridecylsilanol, tridodecylsilanol, tritetradecylsilanol, trioctadecylsilanol, trihexadecylsilanol, trioleylsilanol and trieicosylsilanol; dihexylsilanediol, diheptylsilanediol, diisoheptylsilanediol, dioctylsilanediol, diisooctylsilanediol, di-(ethyl-2-hexyl)-silanediol, di-(sec-octyl)-silanediol, di-(tert-octyl)-silanediol, dinonylsilanediol, diisononylsilanediol, di-decylsilanediol; hexylsilanetriol-heptylsilanetriol, isoheptylsilanetriol, octylsilanetriol, isooctylsilanetriol, 2-ethyl-hexyl-silanetriol, sec-octylsilanetriol, tert-octylsilanetriol, nonylsilanetriol, isononylsilanetriol, decylsilanetriol; silanolcycloaliphatics having 3 to 20 carbon atoms for example: tricyclopropylsilanol, tricyclobutylsilanol, tricyclopentylsilanol, tricyclohexylsilanol, tricycloheptylsilanol, tricyclooctylsilanol, tri-cyclododecylsilanol, tripropylcyclohexylsilanol, trimethylcyclohexylsilanol, and trimethylcycloheptylsilanol; dicyclopropylsilanediol, dicyclobutylsilanediol, dicyclopentylsilanediol, dicyclohexylsilanediol, dicycloheptylsilanediol, dicyclooctylsilanediol, dipropylcyclohexylsilanediol, dimethylcyclohexylsilanediol and dimethylcycloheptylsilanediol; cyclopropylsilanetriol, cyclobutylsilanetriol, cyclopentylsilanetriol, cyclohexylsilanetriol, cycloheptylsilanetriol, cyclooctylsilanetriol, propylcyclohexylsilanetriol, methylcyclohexylsilanetriol and methylcyclohexylsilanetriol and methylcycloheptylsilanetriol; an aromatic silanol or alkyl aromatic silanol having 6 to 20 carbon atoms, for example triphenylsilanol, tribenzylsilanol, triphenylethylsilanol, triphenylpropylsilanol, triphenylocatadecylsilanol and trinaphthyl-decylsilanol; diphenylsilanediol, dibenzylsilanediol, diphenylethylsilanediol, diphenylpropylsilanediol; phenylsilanetriol, benzylsilanetriol, phenylethylsilanetriol, phenylpropylsilanetriol, naphthylsilanetriol (some triols that are too unstable, can be used in their ether forms).

Exemplary of alkanolamines that the present invention may employ are: monoethanol amine, diethanol amine, triethanol amine, alkyl alkanolamines such as ethyl diethanol amine, diethyl ethanol amine, etc.

A typical process of the present invention for preparing cerium (III) alkoxy compounds of formula I:

$$X_1O-\underset{\underset{OX_3}{|}}{Ce}-OX_2 \qquad I$$

comprises reacting suitable alcohol, silanol or alkanolamine with cerous nitrate ammonium nitrate complex in the presence of a base. Groups $OX_1$, $OX_2$ and $OX_3$ are independently selected from the group consisting of:

(a) $NO_3$;
(b) OR;
(c) $OSi(R')_y$; and (d) 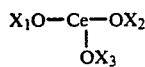

Group R being the same or different and being a substituted or unsubstituted hydrocarbon having 1 to twenty carbon atoms. Group R' being the same or different and being a substituted or unsubstituted hydrocarbon having 1 to 20 carbon atoms or being a hydrogen atom. None, one or two of $OX_1$, $OX_2$ and $OX_3$ are group (a) while the remaining three, two or one, are the same or different and are any of the group (b), (c) or (d), wherein y is 1, 2, or 3, x and z are independently 0, 1 or 2 and $x+y+z=3$; or any two $X_1$, $X_2$ or $X_3$ are represented by a single group having the formula:

(e) 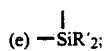

(f) 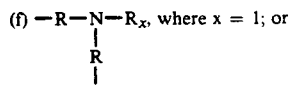

(g) 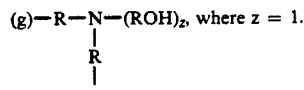

When y=2 the silicon in (c) and the nitrogen in (d) are each linked to two of the oxygens as in (e), (f) or (g), in either (1) the same cerium atom, in which the species are monomeric, or (2) a different cerium atom, in which they are oligomers or polymers.

Preferably, the cerous nitrate ammonium nitrate complex is prepared by reducing ceric ammonium nitrate with ammonia or alcohol. Examples of a base for the above process include ammonia, an alkali metal salt of the alcohol, or an alkali metal salt of the silanol.

The present invention also includes a cerium compound prepared by the above process. The compound having the following formula I:

$$X_1O-\underset{\underset{OX_3}{|}}{Ce}-X_2. \qquad I$$

Groups $OX_1$, $OX_2$ and $OX_3$ are independently selected from the group consisting of (a) $OSi(R')_y$, wherein R' has 1 to 20 carbon atoms or is a hydrogen atom; and (b)

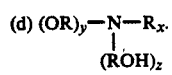

wherein R has 1 to 20 carbon atoms. Parameter y is 1, 2 or 3, x=0, 1 or 2, z=0, 1 or 2 and $x+y+z=3$. Any two $X_1$, $X_2$ or $X_3$ of the above groups may be represented by a single group having the formula:

(c) 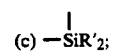

(d) 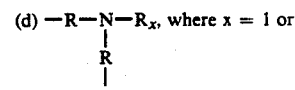

(e) 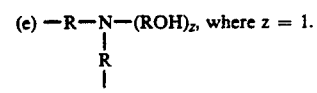

If the molecule employs group (c), then the number of groups (c) is 1, 2 or 3. When y=2, the silicon in (a) and the nitrogen in (b) are each linked to two of the oxygens of $OX_1$, $OX_2$, or $OX_3$ as in (c), (d) or (e), in either:

(1) the same cerium atom, in which the species are monomeric, or (2) a different cerium atom, in which they are oligomers or polymers.

The following examples are for illustration only and do not limit the scope of the invention.

The presence or absence of $Ce^{+4}$ was determined by adding barium diphenylamine sulfate to a sample acidified with glacial acidic acid. When $Ce^{+4}$ is present, the solution shows an intense purple color.

EXAMPLE 1

Reduction of CAN with ammonia in pentane 70.5 g (0.128 mol.) of previously dried CAN (yellow-orange were suspended in 500 ml pentane. The inert gas atmosphere was exchanged with ammonia and the whole system stirred well for 24 hours. During this time the reacting material turned colorless, indicating completion of the reduction. The suspension was filtered and the new compound dried at high vacuum and used without further purification for subsequent reactions. Yield: 79.4 g of an off white powder. The product contained coordinated ammonia.

EXAMPLE 2

Reduction of CAN with ammonia in dimethoxyethane 5 g (9.12 mmol.) CAN were dissolved in 60 ml DME, the solution degassed, saturated with ammonia and stirred overnight. By the next morning the suspended solid had completely lost its yellow orange color.

EXAMPLE 3

Reduction of CAN with ammonia, without solvent 5 g (9.12 mmol.) CAN were efficiently stirred without any solvent in ammonia atmosphere for one week. After this time all the CAN had turned colorless. The cerium(IV) test was negative.

EXAMPLE 4

Attempts to isolate non-complexed $Ce(NO_3)_3$

Fractioning extraction with methanol, where $NH_4NO_3$ is sufficiently soluble, failed. The $NH_4NO_3$ appeared strongly bonded to the $Ce(NO_3)_3$. Bound ammonia, however, was completely dissociated from the complex during treatment, which left the base $Ce(NO_3)_3.3NH_4NO_3$ complex. Attempts to separate $NH_4NO_3$ by sublimation in high vacuum above 100° C. resulted in a loss of only $NH_4NO_3$.

EXAMPLE 5

Methoxides and isopropoxides of Ce(III)

Previously dried CAN is dissolved in excess of methanol and exposed to daylight until all the $Ce^{+4}$ is reduced.

An aliquot of the reaction mixture is treated with $NH_3$ gas whereby $Ce(OCH_3)_3$ precipitates. The methoxide is separated from the ammonium nitrate by extraction and washing with methanol or the reaction mixture used without separating in subsequent synthesis.

Another aliquot is subjected to vacuum removal of all excess methanol and acetaldehyde which is a product of the oxidation of methanol by CAN. The remaining solid is mixed with isopropanol and then reacted with sodium isopropoxide to convert the $Ce(NO_3)_3$ to $Ce(OiPr)_3$.

EXAMPLE 6

Cerium(III) Alkanolatoamine derivatives

Aliquots of $Ce(NO_3)_3$—$NH_4NO_3$ complex stirred in methanol are combined with various ratios of the following alkanolamines:
monoethanolamine—(1:1, 1:2, 1:3)
diethanolamine—(1:1, 1:2)
triethanolamine—(1:1)
diethanolamine—(1:1, 1:2, 1:3)

After the addition of ammonia the corresponding alkanolatoamines are obtained, via exchange with the in situ produced $Ce(OCH_3)_3$.

EXAMPLE 7

3.44 grams CAN with 46.4 grams DME were refluxed overnight. The next day, there was no $Ce^{+4}$ remaining in the flask. The resulting pH was 4.0 indicating that freed $HNO_3$ did react with the oxidation by-products.

EXAMPLE 8

5.0 grams CAN with 50 ml DME were mixed in the presence of 0.4 g charcoal catalyst. All $Ce^{+4}$ were reduced in less than 1.5 hours, and final pH was 1.0.

EXAMPLE 9

In argon atmosphere, 5.0 grams CAN with 45.6 g methanol were mixed at room temperature by stirring in the presence of 0.06 g Platinum/Carbon catalyst. Complete reduction was achieved in 30 minutes, and final pH was 1.0.

EXAMPLE 10

5.0 g CAN, 45 g isopropylalcohol and 0.06 g 5% Ruthenium/Carbon catalyst were stirred at room temperature in an argon atmosphere. Complete reduction of $Ce^{+4}$ was observed in 2 hours.

EXAMPLE 11

2.0 g CAN mixed with 20 cc methanol was exposed to sunlight for one day. Complete reduction occurred.

EXAMPLE 12

The procedure described in Example 11 was repeated with the exception that methanol is replaced by isopropanol, and similar results were obtained.

EXAMPLE 13

The procedure described in Example 11 was repeated with the exception that UV light is substituted for sunlight, and similar results were achieved.

EXAMPLE 14

5.0 CAN, 44.7 g n-butanol and 0.06 g 5% Ruthenium/Carbon catalyst were mixed. Complete reduction was achieved in 1½ hours.

EXAMPLE 15 THROUGH 39

Various trivalent lanthanide nitrate-ammonium nitrate complexes were prepared by mixing aqueous solutions of the nitrates listed below with various amounts of ammonium nitrate. The products of the reaction were evaporated to dryness (with stirring if necessary to effect uniform drying) and then dried under vacuum under the conditions specified below. The corresponding lanthanide nitrate ammonium nitrate complexes were obtained.

| Example No. | Metal | Ratio M(NO₃)₃: NH₄NO₃ | Drying Temperature °C. | Time Hours | Water Content weight % |
|---|---|---|---|---|---|
| | | | At 135 mm of Mercury | | |
| 15 | La | 1:1 | 70 | 20 | Nil |
| 16 | Ce | 1:1 | 70 | 20 | 2.1 |
| 17 | Ce | 1:1 | 70 | 40 | 2.1 |
| 18 | Ce | 1:1 | 70 | 60 | 1.5 |
| 19 | Pr | 1:1 | 70 | 20 | 0.3 |
| 20 | Pr | 1:1 | 70 | 40 | Nil |
| 21 | La | 1:2 | 90 | 0 | 0.88 |
| 22 | La | 1:2 | 90 | 60 | Nil |
| 23 | Ce | 1:2 | 90 | 0 | 1.56 |
| 24 | Ce | 1:2 | 90 | 60 | Nil |
| 25 | Pr | 1:2 | 90 | 0 | 3.35 |
| 26 | Pr | 1:2 | 90 | 60 | Nil |
| 27 | Nd | 1:2 | 90 | 0 | 0.55 |
| 28 | Nd | 1:2 | 90 | 60 | Nil |
| 29 | Y | 1:1 | 110 | 48 | 15.5 |
| 30 | Y | 1:1 | 110 | 70 | 6.9 |
| 31 | Y | 1:2 | 110 | 48 | 1.08[1] |
| 32 | Y | 1:2 | 110 | 70 | 0 |
| 33 | Y | 1:3 | 110 | 48 | 1.77[1] |
| 34 | Y | 1:3 | 110 | 70 | 0 |
| 35 | La | 1:3 | 90 | 15 | Nil |
| 36 | Ce | 1:3 | 90 | 15 | Nil |
| 37 | Pr | 1:3 | 90 | 24 | Nil |
| 38 | Nd | 1:3 | 90 | 24 | Nil |
| | | | At 0.01 mm of Mercury | | |
| 39 | Ce | 1:2 | 50 | 3 | Nil |

[1]Material extremely hydroscopic, Humidity pickup during analysis possible.

As a control, hydrated La(NO₃)₃ without ammonium nitrate was dried for 200 hours at 95° C. under a vacuum of 135 mm of mercury. The product still contained 5.47% water. In contrast, a lanthanum nitrate with ammonium nitrate (1:1 ratio) dried to a water content of "Nil" at 70° C. after only 20 hours under 135 mm mercury (See Example 15).

EXAMPLE 40

Reaction of cerium(III) nitrate with sodium isopropoxide

To a fresh prepared suspension of cerium(III) nitrate complex (1.85 mmol) in DME were added 11.1 mmol (4.17 ml of a 2.66 molar solution) of NaOiPr in isopropanol. After 2 hours the reaction mixture was filtered, yielding 801 mg NaNO₃ = 85.0% of the expected NaNO₃ (some solid remained on the walls of the frit). The filtrate was dried, slurried up in pentane and filtered. Yield: 810 mg (1.63 mmol)=88.1% for Ce(OiPr)₃(HOiPr)₃ (M.W.=497.67).

The nmr spectra was essentially identical to the one taken from a compound prepared independently by reaction of CeCl₃ with NaOiPr in THF/IPA (tetrahydrofuran/isopropyl alcohol).

EXAMPLE 41

Reaction of the cerous nitrate complex with triphenylsilanol

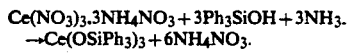

5 g of Ce(NO₃)₃.3NH₄NO₃ were suspended in 40 ml (35 g) of DME. 7.32 g of Ph₃SiOH were added as a solid and stirred for five minutes. In the next five minutes NH₃ gas was bubbled through the suspension forming a light yellow clear upper phase. Addition of NH₃ gas was continued in the next 10 minutes. Subsequent filtration of the mixture using a shlenk frit yielded a clear, light yellow filtrate. After removing the solvent at oil-pump vacuum, 5.8 g of a white powder was obtained.

Good solubility in CHCl₃, DME, THF.
¹H NMR (CHCl₃-d) 7.24; 7.59
¹³C NMR (CHCl₃-d) 127.76; 129.93; 134.91

EXAMPLE 42

Reaction of Y(NO₃)₃.4NH₄NO₃ with KOC(CH₃)₃

3.98 g (0.0355 m) of potassium tert-butoxide was dissolved in 60 ml THF. To the clear, almost colorless solution was added 3 g (0.00507 m) of Y(NO₃)₃.4NH₄NO₃ as a solid. Immediately on stirring, an exothermic reaction began, and formation of NH₃ gas was observed. The mixture was stirred overnight and, by subsequent filtration, 3.40 g of a white KNO₃ powder was recovered (theory 3.58 g). The clear, pale orange filtrate was evaporated to dryness to give a tan colored powder.

Yield 1.4 g=89.6% for Y(OC(CH₃)₃)₃.
Soluble in most organic solvents.
The ¹H NMR shows in CHCl₃-d a main singlett at 1.21 ppm and two smaller signals at 1.36 and 1.59 ppm.

EXAMPLE 43

Reaction of Y(NO₃)₃.4NH₄NO₃ with 7NaO(CH₂)₃N(CH₃)₂

To 2 g (3.36 mmol) Y(NO₃)₃.NH₄NO₃ in 30 ml THF were added 67 ml (23.5 mmol) of a 0.35M solution of NaO(CH₂)₃N(CH₃)₂ in toluene. The solution was stirred overnight, filtered and washed with 20 ml of toluene.

Isolated 1.93 g (22.7 mmol) NaNO₃ (still contained 23 mg of Y as ash).

Yield: 1.19 g (3.01 mmol)=89.6% for Y[O(CH₂)₃N(CH₃)₂]₃

EXAMPLE 44

Reaction of Y(NO₃)₃.4NH₄NO₃ with 7(CH₃CH₂)₂N(CH₂)₂ONa

To 2.17 g (3.65 mmol) Y(NO₃)₃.4NH₄NO₃ and 3.56 g (25.56 mmol) NaO(CH₂)₂N(CH₂CH₃)₂ were added 50 ml THF. The reaction mixture was stirred overnight, filtered and the precipitate washed 3 times with 2-4 ml THF, and the solvent removed from the filtrate.

Isolated 1.94 g (22.83 mmol) NaNO₃=89.3%.
Yield 856 mg (1.96 mmol) Y[OCH₂CH₂N(CH₂CH₃)₂]₃=53.7%.

Same as above:
To 1.70 g (2.85 mmol) of Y(NO₃)₃.4NH₄NO₃ and 2.78 g (19.94 mmol) NaO(CH₂)₂N(CH₂CH₃)₂ at −78° C. were added 50 ml precooled THF. The reaction began below 0° C. It was allowed to react overnight, filtered and the precipitate washed with THF, and the solvent removed.

Isolated: 1.31 g (15.4 mmol)NaNO₃=77%.
Yield: 1.02 g (2.3 mmol) Y[OCH₂CH₂N(CH₂CH₃)₂]₃=82%.

EXAMPLE 45

Reaction of La(NO$_3$)$_3$.NH$_4$NO$_3$ with 4NaOCH$_2$CH$_2$N(CH$_2$CH$_3$)$_2$ To 1.97 g (5.06 mmol) La(NO$_3$)$_3$.NH$_4$NO$_3$ were added 90 ml of a 0.225M (20.25 mmol) toluene solution of NaOCH$_2$CH$_2$N(CH$_2$CH$_3$)$_2$. Because the reaction did not seem to proceed in toluene, it was partially removed (50 ml remained) and 20 ml THF added. The mixture was allowed to react over night, filtered, the precipitate washed, and the solvent removed from the filtrate.

Isolated: 1.67 g NaNO$_3$ (19.6 mmol)=97.1%.

A small amount of product was found with the sodium nitrate (equivalent to 35.4 mg La$_2$O$_3$ that was found by ash analysis).

EXAMPLE 46

Reaction of Ce(III) Ammonium Nitrate with Sodium 2-diethylaminoethanolate in THF 3 g (5.16 mmoles) of Ce(NO$_3$)$_3$2.5NH$_4$NO$_3$×DME (FW=580.86 g) were partially dissolved in 150 ml THF. 3.96 g (28.42 mmoles) of 2-ethylamino sodium ethanolate, dissolved in 30 ml THF, were added dropwise to the solution under stirring. A white precipitate occurred immediately under evolution of ammonia. When ⅔ of the solution were added the reaction mixture turned slightly yellow and then slowly white again, when all the salt was added. The reaction mixture was heated to approximately 60° C. overnight under stirring and filtered, yielding 2.3 g of sodium nitrate. The solvent was removed from the filtrate under reduced pressure at room temperature, yielding a light yellow oil. The oil was very air sensitive. (Turned to green then brownish in one minute when exposed to air).

Precipitate: 2.3 g NaNO$_3$ (27.1 mmol.) i.e. 95% containing only traces of cerium.

Filtrate: No nitrates were detected.

Soluble in MeOH, C$_6$H$_6$, THF, and pentane.

Yield: 96%

EXAMPLE 47

Reaction of Ce(III) Ammonium Nitrate with Disodium 2-ethylamino-diethanolate in THF 2.197 g (4.51 mmoles) of Ce(NO$_3$)$_3$2NH$_4$NO$_3$ were partially dissolved in 150 ml THF. 2 g (11.3 mmoles) of disodium salt dissolved in 60 ml THF were added slowly to the solution under stirring. Evolution of ammonia was observed. A white precipitate occurred. The reaction mixture was allowed to stir overnight. The mixture was filtered, yielding 1.97 g of sodium nitrate (quantitative yield). The filtrate was evaporated to dryness, yielding 1.945 g of a pale white powder.

cerium content 29 43%, yield 91% theoretical cerium content: 29.54%

The compound is air sensitive; s in THF, CDCl$_3$, and MeOH, and i in pentane and i-PrOH

EXAMPLE 48

Reactions of Ce(III) Ammonium Nitrate with the Lithium Salts of Alkanolamines

Reaction of (NH$_4$)$_2$Ce(NO$_3$)$_5$ with Dilithium 2-Aminoethanolate.

To 3 g (6.17 mmoles) of Ce(NO$_3$)$_3$2NH$_4$NO$_3$ partially dissolved in 150 ml THF was added dropwise a solution of 2.23 g (15.43 mmoles) of the dilithium salt in THF into the reaction flask. After 5 minutes of stirring everything went into solution. The solution turned light yellow under evolution of ammonia. The solution was stirred overnight. The solvent was removed and exchanged against acetonitrile. The reaction mixture was filtered yielding 1.4 g of LiNO$_3$ (65.8%). The filtrate was evaporated to dryness, yielding 2.62 g of a greenish powder. Yield 79%.

EXAMPLES 49-61

Examples 49-53 describe the preparation of Ln(III)-tris (triphenylsilyloxides) by reaction of anhydrous Ln(NO$_3$)$_3$×NH$_4$NO$_3$ with NaOSiPh$_3$, e.g.:

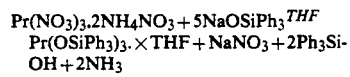

After filtering off the NaNO$_3$, the product precipitates out of the THF solution as a THF-adduct. The two moles of Ph$_3$SiOH, formed during the reaction, remain in solution.

Examples 54-61 describe the reaction of the anhydrous nitrates with the disodium salts of Ph$_2$Si(OH)$_2$ or tetramethyldisiloxanol: e.g.:

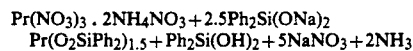

In these reactions the products do not precipitate out of the reaction filtrates, as it is in Example 49-61. They are obtained by evaporating the reactions solution to dryness. One side reaction occurs, when the 1 mole of Ph$_2$Si(OH)$_2$, formed during the reaction, undergoes partial condensation to form water, which in the presence of NH$_3$ hydrolizes the lanthanide nitrate and forms insoluble Ln(OH)$_3$. Nevertheless, the main part of the Ln(NO$_3$)$_3$ complex is not hydrolized and forms definitely a Ln-O-Si product.

EXAMPLES 49-53

General Procedure For the Preparation of Ln(III)-tris (triphenylsilyloxides)

The anhydrous metal nitrate and NaOSiPh$_3$ THF were placed in a Schlenk flask in stoichiometric ratio as solids and charged with 40 ml THF. Immediately on stirring, formation of NH$_3$ gas was observed and stirring was continued overnight. In a subsequent work-up the white precipitate (NaNO$_3$) was filtered using a Schlenk frit and washed with 20 ml of THF. The combined clear filtrates were concentrated at oil pump vacuum down to a volume of circa 40 ml and stored overnight at −30° C. to give shiny, transparent crystals. They were isolated by filtration and dried gently at oil pump vacuum.

EXAMPLE 49

Ce(NO$_3$)$_3$.2NH$_4$NO$_3$: 3 g (0.00617 m)

Ph$_3$SiONa . THF: 11.42 g (0.0308 m)

Colorless crystals, yield 5 g which equals about 68% for Ce(OSiPh$_3$)$_3$.3THF; m.p 145°-146° C.

Air-sensitive; soluble in CHCl$_3$, THF, DME, toluene.

Analyses: Calc: C. 67.04; H. 5.84 for Ce(O-SiPh$_3$)$_3$.3THF; Found: C. 67.06; H. 5.99.

Amount of NaNO$_3$ recovered=1.70 g

Theory for 5NaNO$_3$=1.75 g

NMR results: $^1$H NMR (CHCl$_3$-d) 0.66 (s,24); 7.30, 9.55 (s,s,45) $^{13}$C NMR (CHCl$_3$-d) 23.75; 61.07; 127.71; 128.57; 136.32; 146.51.

EXAMPLE 50

Pr(NO$_3$)$_3$2NH$_4$NO$_3$: 2 g (0.00411 m)
Ph$_3$SiONa.0.75 THF: 7.31 g (0.0205 m)

Light green crystals, yield 2.5 g which equals about 50% for Pr(OSiPh$_3$)$_3$.3THF; m.p. 130°–132° C.

Air-stable, but crystals decay in air. Soluble in toluene, CH$_3$CN, THF, CHCl$_3$, insoluble in pentane.

Analyses: Calc: C. 66.99; H. 5.84 for Pr(OSiPh$_3$)$_3$ . 3THF; Found: C. 67.20, H. 6.24.

Amount of NaNO$_3$ recovered 1.73 g
Theory for 5NaNO$_3$: 1.74 g

NMR results: $^1$H NMR (CHCl$_3$-d) 8.34; 8.71; 16.53 (s,45); −7.48 (S,12), −15.08 (S,12) $^{13}$C NMR (CHCl$_3$-d) 130.52; 143.54; 161.75; 29.66; 11.45.

EXAMPLE 51

Nd(NO$_3$)$_3$.2NH$_4$NO$_3$: 1.8 g (0.00367 m)
NaOSiPh$_3$.THF: 6.8 g (0.0183 m)

Blue crystals, yields 3 g which equals about 69% for Nd(OSiPh$_3$)$_3$ 3THF; m.p. 140°–142° C. Air-stable, but crystals decay in air. Soluble in toluene, CH$_3$CN, THF, CHCl$_3$; insoluble in pentane.

Amount of NaNO$_3$ recovered: 1.52 g
Theory for 5 NaNO$_3$: 1.56 g

Analyses: Calc. C. 66.81; H. 5.82 for Nd(OSiPH$_3$)$_3$ 3THF; Found C. 66.61; H. 6.15.

NMR results: $^1$H NMR (CHCl$_3$-d) 7.23; 8.73 (m,45); −0.38; −1.07 (S,24) $^{13}$C NMR (CHCl$_3$-d) 127.60; 129.22; 135.62; 58.91; 22.61.

EXAMPLE 52

Y(NO$_3$)$_3$.4NH$_4$NO$_3$: 1.5 g (0.00253 m)
Ph$_3$SiONa . 0.75 THF: 6.33 g (0.0177 m)

Colorless crystals, yield 2 g which equals about 65% for Y(OSiPh$_3$)$_3$.4THF; m.p. 135°–136° C. Air-stable, soluble in toluene, THF, CHCl$_3$, insoluble in CH$_3$CN and pentane.

Analysis: Calc: C. 69.87, H. 6.40 for Y(OSiPh$_3$)$_3$ . 4THF; Found: C. 69.98; H. 6.48.

Amount of NaNO$_3$ recovered: 1.51 g
Theory for 7 NaNO$_3$: 1.50 g

NMR results: $^1$H NMR (CHCl$_3$-d) 1.56 (s,16), 3.65 (s,16); 7.22; 7.57 (m, 45) $^{13}$C NMR (CHCl$_3$-d) 25.21; 69.04; 127.33; 128.68; 135.02; 139.63.

EXAMPLE 53

La(NO$_3$)$_3$ . 2.5 NH$_4$NO$_3$: 0.75 g (0.0014 m)
Ph$_3$SiONa . THF: 2.9 g (0.0078 m)

Colorless crystals, yield 1 g which equals about 60.5% for La(OSiPh$_3$)$_3$ . 3THF, m.p. 95° C.

Air-stable; soluble in toluene, CHCl$_3$, DME, i-PrOH; insoluble in ethylene glycol.

Analyses: Calc: C. 67.11; H. 5.84; Found: C. 69.42; H. 5.83.

Amount of NaNO$_3$ recovered: 0.638 g
Theory for 5.5 NaNO$_3$: 0.665 g

NMR Results: $^1$H NMR (CHCl$_3$-d) 1.52; 3.58; 7.22; 7.51(m) $^{13}$C NMR (CHCl$_3$-d) 25.21; 68.76; 127.49; 129.11; 135.02; 138.00.

EXAMPLES 54–61

General Procedure for the Preparation of Ln (III)-diphenylsilyloxides and Ln(III)-tetraphenyldisiloxanes The anhydrous metal nitrate and the disodium salts of either Ph$_2$Si(OH)$_2$ or tetramethyldisiloxanol were placed in a Schlenk flask in stoichiometric ratio as solids and charged with 40 ml THF. Immediately on stirring formation of NH$_3$ gas was observed and stirring was continued overnight. In a subsequent work-up the precipitate (mainly NaNO$_3$) was filtered using a Schlenk frit and washed with 20 ml THF. The combined clear filtrates were evaporated to dryness at oil pump vacuum with heating (about 40° C.) to give fine powders.

EXAMPLE 54

Ce(NO$_3$)$_3$ . 2NH$_4$NO$_3$: 2 g (0.004114 m)
Ph$_2$Si(ONa)$_2$ . 2THF: 4.15 g (0.010 m)

Pale yellow, air-sensitive powder, yield 3.3 g which equals about 97% for Ce(O$_2$SiPh$_2$)$_{1.5}$. Ph$_2$Si(OH)$_2$ . 2THF; soluble in most organic solvents, m.p. 300° C.

NMR Results: $^1$H NMR (CHCl-d) 1.82(THF), 3.89(THF); 6.12(s), 7.11(m), 7.51(d), 8.74(d); 9.10(s), 12.41. $^{13}$C NMR (CHCl$_3$-d) 25.64(THF); 68.38(THF); 125.76; 126.98 128.69; 130.07; 131.77; 134.54; 137.06; 138.44; 143.89.

Due to the paramagnetism of Ce(III), the NMR spectra are relatively complex, showing an unusually high number of signals for the phenyl signals.

EXAMPLE 55

Pr(NO$_3$)$_3$ . 2NH$_4$NO$_3$: 1 g (0.00205 m)
Ph$_2$Si(ONa)$_2$ . 2THF: 2 g (0.00513 m)

Green, yellow fine powder, yield 1.3 g which equals about 59% for Pr(O$_2$SiPh$_2$)$_{1.5}$ . Ph$_2$Si(OH)$_2$ . 2THF; moderately air-sensitive; does not have a definite melting point, becomes a viscous mass around 120° C.; very soluble in toluene, CH$_3$CN, THF, CHCl$_3$, insoluble in pentane.

NMR Results: $^1$H NMR (CHCl$_3$-d) 1.19(THF); 5.76(s); 6.29(t); 8.73(m); 11.39(d). $^{13}$C NMR (CHCl$_3$-d) 24.67 (THF); 66.06 (THF); 126.08; 127.27; 129.98; 130.96; 137.67; 140.06; 142.88.

EXAMPLE 56

Nd(NO$_3$)$_3$ . 2NH$_4$NO$_3$: 1 g (0.00203 m)
Ph$_2$Si(ONa)$_2$ . 2THF: 2.06 g (0.005075 m)

Pale blue powder, air-stable, yield 1.3 g which equals about 77.84% for Nd(O$_2$SiPh$_2$)1.5 . Ph$_2$Si(OH)$_2$ . 2THF; m.p. and solubilities like Example 55.

NMR Results: $^1$H NMR (CHCl$_3$-d) 1.54(THF); 3.27; 5.56(s,br); 6.34(s); 6.69(s); 7.88(s); 9.29(s). $^{13}$C NMR (CHCl$_3$-d) 25.27; 67.46; 126.78; 127.92; 128.79; 130.31; 132.42; 135.73; 142.11.

EXAMPLE 57

Y(NO$_3$)$_3$ . 4NH$_4$NO$_3$: 0.75 g (0.00169 m)
Ph$_2$Si(ONa)$_2$ . 2THF: 1.75 g (0.00592 m)

Bright, light yellow powder, yield 1 g which equals about 76.9% for Y(O$_2$SiPh$_2$)$_{1.5}$ . Ph$_2$Si(OH)$_2$ . 2THF; m.p. and solubilities like Example 55.

NMR Results: $^1$H NMR (CHCl$_3$-d) 1.57(THF); 3.31(THF); 7.13(m). $^{13}$C NMR (CHCl$_3$-d) 25.32(THF); 67.63(THF); 127.22; 133.94; 134.75; 139.30; 141.20.

In the following, the disodium salt of tetramethyldisiloxanol is abbreviated as TMDS.

EXAMPLE 58

Ce(NO$_3$)$_3$ . 2NH$_4$NO$_3$: 1.48 g (0.00304 m)
TMDS: 2.5 g (0.00762 m)

Pale yellow, air-sensitive powder, yield 0.75 g which equals about 45% for

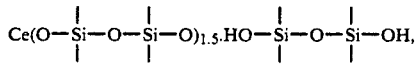

m.p. greater than 200° C. (decomposes); soluble in THF, moderately soluble in toluene and CHCl₃, insoluble in pentane, CH₃CN, i-PrOH.

NMR Results: $^1$H NMR (THF-d$_8$) 0.1497; $^{13}$C NMR (THF-d$_8$) 1.35.

EXAMPLE 59

Nd(NO$_3$)$_3$ . 2NH$_4$NO$_3$: 1.49 g (0.00304 m)
TMDS: 2.5 g (0.00762 m)
Pale blue powder, air-stable; yield 1 g which equals about 60% for

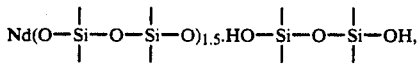

m.p. greater 240° C. (decomposes), soluble in THF, CHCl₃, toluene; insoluble in pentane, CH₃CN and i-PrOH.

NMR Results: $^1$H NMR (CHCl₃-d) 1.81(THF); 3.77(THF); 0.09 $^{13}$C NMR (CHCl₃-d) 25.64(THF); 68.06(THF); 1.05.

EXAMPLE 60

Pr(NO$_3$)$_3$ . 2NH$_4$NO$_3$: 1.48 g (0.00305 m)
TMDS: 2.5 g (0.00762 m)
Pale green powder, decays in air, yield 1 g which equals about 59.5% for

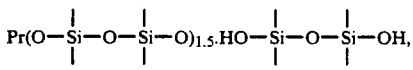

m.p. 140° C. (decomposes); soluble in THF, CHCl₃, CH₃CN, toluene; slightly soluble in pentane, insoluble in i-Pr-OH.

NMR Results: $^1$H NMR (CHCl₃-d) 1.94(THF); 3.97(THF); 0.09 $^{13}$C NMR (CHCl₃-d) 25.64(THF); 68.11(THF); 0.72

EXAMPLE 61

Y(NO$_3$)$_3$ . 4NH$_4$NO$_3$: 1.42 g (0.00239 m)
TMDS: 2.5 g (0.00839 m)
Light yellow powder, air-stable, yield 0.5 g which equals about 41.9% for

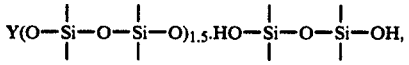

soluble in CHCl₃, THF, toluene, pentane, CH₃CN, i-PrOH.

NMR Results: $^1$H NMR (CHCl₃-d) 0.34 $^{13}$C NMR (CHCl₃-d) 0.78

The above is intended to exemplify and explain the present invention, it is not intended to limit the spirit and scope of the present invention which is defined by the claims appended hereto.

We claim:

1. A process for preparing a trivalent Group 3b metal alkoxy compound, at least a portion of a molecule of the compound having formula I:

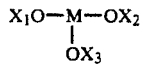

which comprises reacting an anhydrous complex of a nitrate of a trivalent metal of Group 3b and a nitrate selected from ammonium nitrate or an alkali metal nitrate, with an alcohol, silanol or alkanolamine, as defined below, in the presence of a base, or reacting said complex with an alkali metal salt of said alcohol, silanol or alkanolamine wherein M is a trivalent metal of Group 3b, X$_1$, X$_2$ and X$_3$ are independently selected from the group consisting of:

(a) —NO$_2$;

(b) —R, wherein R is a saturated or unsaturated hydrocarbon and has 1 to 20 carbon atoms;

(c) —Si(R')$_3$, wherein each R' is independently a saturated or unsaturated hydrocarbon having 1 to 20 carbon atoms or an alkoxy group having 1 to 10 carbon atoms;

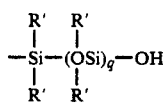

wherein q is zero to about 1000; and

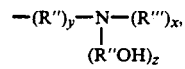

wherein each R" is independently a hydrocarbon having 1 to 20 carbon atoms, wherein each R'" is independently a hydrocarbon having 1 to 20 carbon atoms or a hydrogen atom;

wherein R, R', R", and R'" are independently saturated or unsaturated;

y represents 1 and x and z independently represent 0, 1 or 2 and x+y+z equals 3; or any two X$_1$, X$_2$ and X$_3$ are represented by a single group selected from:

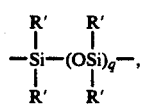

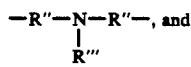

any three X$_1$, X$_2$ and X$_3$ are represented by a single group selected from:

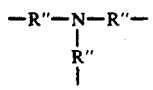 (i)

wherein (f), (g) or (h) link to two oxygen atoms, or (i) links to three oxygen atoms, attached to either:
(1) the same atom of the trivalent metal of Group 3b of formula I such that the compound is monomeric, or
(2) more than one atom of the trivalent metal of Group 3b arranged as in formula I, such that the compound is an oligomer or a polymer;

wherein at most two of $X_1$, $X_2$ or $X_3$ of formula I are substituent (a);
wherein the alcohol is HO—(b);
wherein the silanol is HO—(c) or HO—(d); and
wherein the alkanolamine is HO—(e).

2. The process according to claim 1, wherein the Group 3b metal is cerium and the complex is cerous nitrate ammonium nitrate complex, the complex is prepared by reducing ceric ammonium nitrate with anhydrous ammonia.

3. The process according to claim 1, wherein the Group 3b metal is cerium and the complex is cerous nitrate ammonium nitrate complex, the complex is prepared by reducing ceric ammonium nitrate with alcohol in the presence of sufficient ultraviolet irradiation or catalyst to effect the reduction.

4. The process according to claim 1, wherein the base is ammonia.

5. The process according to claim 1, wherein the base is an alkali metal salt of the alcohol.

6. The process according to claim 1, wherein the base is an alkali metal salt of the silanol.

7. The process according to claim 1, wherein the complex is anhydrous and is prepared by combining a trivalent Group 3b metal nitrate with ammonium nitrate or an alkali metal nitrate to form a mixture, followed by drying the mixture to remove water of coordination to form the anhydrous complex.

8. The process according to claim 7, wherein the Group 3b metal nitrate is combined with ammonium nitrate.

9. The process according to claim 7, wherein the Group 3b metal nitrate is combined with the alkali metal nitrate and the alkali metal nitrate is sodium nitrate.

10. The process according to claim 9, wherein the anhydrous complex is reacted with a sodium salt of the alcohol, silanol or alkanolamine to form a sodium nitrate precipitate and recycling it as starting material in the synthesis of additional anhydrous complex.

11. The process according to claim 7, wherein said ammonium nitrate or alkali metal nitrate is used in a molar ratio to said trivalent Group 3b metal nitrate ranging from about 1:1 to about 5:1.

12. The process according to claim 7, wherein said complex is dehydrated at a temperature ranging from about 50° C. to about 160° C. under vacuum.

13. The process according to claim 12, wherein said complex is dehydrated at a temperature ranging from about 80° C. to about 130° C.

14. The process according to claim 12, wherein said complex is dehydrated under vacuum of less than 300 millimeters of mercury.

15. The process according to claim 12, wherein said complex is dehydrated under vacuum of less than 100 millimeters of mercury.

16. The process according to claim 7, wherein said trivalent Group 3b metal is a lanthanide having an atomic number ranging from 57 to 60.

17. The process according to claim 7, wherein said trivalent Group 3b metal is yttrium.

18. The process according to claim 7, wherein R is straight, branched or cycloaliphatic, R' has 1 to 6 carbon atoms, R" is ethyl, and R'" is ethyl, methyl or a hydrogen atom.

19. The process according to claim 1, wherein the trivalent group 3b metal alkoxy compound has the formula:

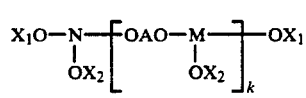 II wherein k is selected such that the compound is an oligomer or polymer and A is (e), (f) or (g).

20. A compound prepared by a process comprising the steps of;
reacting suitable silanol or alkanolamine, as defined below, with cerous nitrate ammonium nitrate complex in the presence of a base, further comprising preparing the cerous nitrate ammonium nitrate complex by reducing ceric ammonium nitrate with anhydrous ammonia, as defined below, in the presence of sufficient ultraviolet irradiation or sufficient catalyst to effect the reduction,
the compound being a cerium (III) alkoxy compound, at least a portion of a molecule of the compound having formula I:

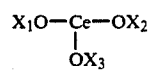 I wherein $X_1$, $X_2$ and $X_3$ are independently selected from the group of substituents consisting of:
(a) —$SiR'_y$, wherein y is 3 and R' has 1 to 20 carbon atoms or is a hydrogen atom; and

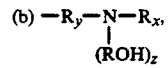

wherein R has 1 to 20 carbon atoms,
wherein y is 1, x=0, 1 or 2, z=0, 1 or 2 and x+y+z=3; or
any two $X_1$, $X_2$ or $X_3$ are represented by a single substituent having the formula:

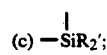

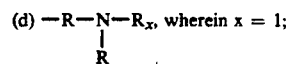

-continued (e) 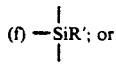 wherein z = 1; or any three $X_1$, $X_2$ or $X_3$ are represented by a single substituent having the formula:

(f) 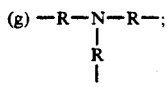 or (g) —R—N—R—;
      |
      R
      | wherein (c), (d) or (e) is linked to two oxygen atoms, or (f) or (g) link to three oxygen atoms, attached to either:
(1) the same cerium atom of formula I, such that the compound is monomeric, or
(2) more than one cerium atom arranged as in formula I, such that the compound is an oligomer or polymer
wherein the silanol has the formula
OH—(a),
$(OH)_2$—(c), or
$(OH)_3$—(f); and
wherein the alkanolamine has the formula
OH—(b).

21. A process for preparing a cerium (III) alkoxy compound, at least a portion of a molecule of the compound having formula I:

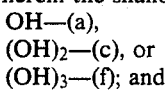         I comprising the steps of:
reacting suitable alcohol, silanol or alkanolamine with cerous nitrate ammonium nitrate complex in the presence of a base, wherein the cerium atom of said complex is trivalent, wherein $X_1$, $X_2$ and $X_3$ are independently selected from the group of substituents consisting of:
(a) —$No_2$;
(b) —R, wherein R has 1 to 20 carbon atoms;
(c) —$SiR'_y$, wherein R' has 1 to 20 carbon atoms or is a hydrogen atom, and y=3;

(d) 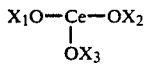

wherein R and R" each have 1 to 20 carbon atoms, x is 0, 1 or 2, y is 1, z is 0, 1 or 2, and x+y+z=3;

(e) 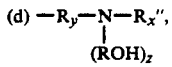

wherein n1 is 1 to 10 and R' has 1 to 20 carbon atoms or is a hydrogen atom; or any two of $X_1$, $X_2$ or $X_3$ are represented by a single substituent selected from the group consisting of:

(f) 

(g) 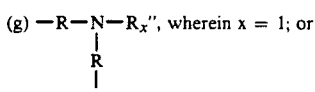

(h) 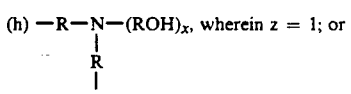

(i) 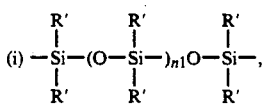

wherein n1 is 1 to 10; or
any three $X_1$, $X_2$ or $X_3$ are represented by a single substituent having the formula:

(j) 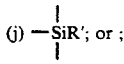

(k) 

wherein (f), (g), (h) or (i) is linked to two oxygen atoms, or (j) or (k) is linked to three oxygen atoms, attached to either:
(1) the same cerium atom of formula I, such that the compound is monomeric; or
(2) more than one cerium atom arranged as in formula I, such that the compound is an oligomer or polymer;
wherein at most two of the group $X_1$, $X_2$ and $X_3$ of formula I are substituent (a);
wherein the alcohol is HO—(b);
wherein the silanol is HO—(c), $(HO)_2$—(f), $(HO)_3$—(j) or HO—(e); and
wherein the alkanolamine is HO—(d).

22. The process of claim 21, wherein $X_1$, $X_2$ and $X_3$ are the same or different and selected from the group consisting of (a); (b); (c); and (d).

23. The process of claim 21, wherein said compound is for formula II:

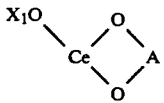   II:

wherein A is selected from said substituent group (f), (g) or (h).

24. The process of claim 21, wherein at least one of said $X_1$, $X_2$ or $X_3$ is selected from (f), (g), (h) or (i) which is linked to said two oxygen atoms attached to more than one cerium atom arranged as in formula I so that said compound is said oligomer or polymer.

25. The process according to claim 21, further comprising preparing the cerous nitrate ammonium nitrate complex by reducing ceric ammonium nitrate with anhydrous ammonia.

26. The process according to claim 21, further comprising preparing the cerous nitrate ammonium nitrate complex by reducing ceric ammonium nitrate with alcohol in the presence of sufficient ultraviolet irradiation or catalyst to effect the reduction.

27. The process according to claim 21, wherein the base is an alkali metal salt of the alcohol.

28. The process according to claim 21, wherein the base is an alkali metal salt of the silanol.

29. A compound prepared by the process of claim 21 the compound being the cerium (III) alkoxy compound of claim 21
   wherein $X_1$, $X_2$ and $X_3$ are independently selected from the group of substituents consisting of (c) and (d): or
   any two of $X_1$, $X_2$ and $X_3$ are represented by a single substituent independently selected from the group of (f), (g), or (h).

30. The process according to claim 21, further comprising preparing the cerous nitrate ammonium nitrate complex by reducing ceric ammonium nitrate with anhydrous ammonia or with said alcohol in the presence of sufficient ultraviolet irradiation or sufficient catalyst to effect the reduction, wherein
   $X_1$, $X_2$ and $X_3$ are independently selected from the group of substituents consisting of (a), (b), (c) and (d);
   or any two $X_1$, $X_2$ and $X_3$ are represented by a single substituent selected from the group of substituents consisting of (f), (g) or (h).

31. The process according to claim 30, wherein the cerous nitrate ammonium nitrate complex is prepared by reducing ceric ammonium nitrate with ammonia.

32. The process according to claim 30, wherein the cerous nitrate ammonium nitrate complex is prepared by reducing ceric ammonium nitrate with said alcohol.

33. The process according to claim 30, wherein the base is ammonia.

34. The process according to claim 30, wherein the base is an alkali metal salt of the alcohol.

35. The process according to claim 30, wherein the base is an alkali metal salt of the silanol.

36. A process for preparing trivalent Group 3b metal alkoxy compounds of formula I:

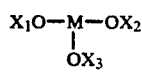

which comprises reacting an anhydrous complex of a nitrate of a trivalent metal of Group 3b and a nitrate selected from ammonium nitrate or an alkali metal nitrate, with an alcohol in the presence of a base, or reacting said complex with an alkali metal salt of said alcohol, wherein
   M is a trivalent metal of Group 3b, and $X_1$, $X_2$ and $X_3$ are independently selected from the group consisting of:
   (a) $NO_2$;
   (b) R, wherein each R is an independently saturated or unsaturated hydrocarbon and has 1 to 20 carbon atoms,
   wherein at most two of the group $X_1$, $X_2$ and $X_3$ of formula I are substituent (a),
   wherein the alcohol has the formula HO—(b).

37. A process for preparing trivalent Group 3b metal alkoxy compounds of formula I:

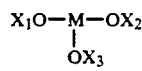

which comprises reacting an anhydrous complex of a nitrate of a trivalent metal of Group 3b and a nitrate selected from ammonium nitrate or an alkali metal nitrate, with a silanol in the presence of a base, or reacting said complex with an alkali metal salt of said silanol, wherein
   M is a trivalent metal of Group 3b, and $X_1$, $X_2$ and $X_3$ are independently selected from the group consisting of:
   (a) $NO_2$;
   (b) $Si(R)_3$, wherein each R is independently a saturated or unsaturated hydrocarbon having 1 to 20 carbon atoms or an alkoxy group having 1 to 10 carbon atoms,
   wherein at most two of the group $X_1$, $X_2$ and $X_3$ of formula I are substituent (a),
   wherein the silanol has the formula $HOSi(R)_3$.

38. The process of claim 37 wherein R is phenyl.

39. A process for preparing trivalent Group 3b metal alkoxy compounds of formula I:

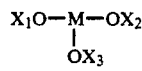

which comprises reacting an anhydrous complex of a nitrate of a trivalent metal of Group 3b and a nitrate selected from ammonium nitrate or an alkali metal nitrate, with an alkanolamine in the presence of a base, or reacting said complex with an alkali metal salt of said alkanolamine wherein
   M is a trivalent metal of Group 3b, and $X_1$, $X_2$ and $X_3$ are independently selected from the group consisting of:
   (a) —$NO_2$; or (a) $NO_2$; or (b) —$R_y''$—N—$(R''')_x$,
         |
         $(R''QH)_z$ wherein each R" is independently a hydrocarbon having 1 to 20 carbon atoms, wherein each R''' is independently a hydrocarbon having 1 to 20 carbon atoms or a hydrogen atom;
   wherein R" and R''' are independently saturated or unsaturated, and
   y represents 1 and x and z independently represent 0, 1 or 2 and x+y+z equals 3;
   wherein at most two of the group $X_1$, $X_2$ and $X_3$ of formula I are substituent (a);
   wherein the alkanolamine has the formula HO—(b).

40. A process for preparing trivalent Group 3b metal alkoxy compounds of formula I:

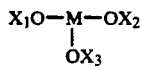

which comprises reacting an anhydrous complex of a nitrate of a trivalent metal of Group 3b and a nitrate selected from ammonium nitrate or an alkali metal nitrate, with an alcohol, silanol or alkanolamine, in the presence of a base, or reacting said complex with an alkali metal salt of said alcohol, silanol or alkanolamine, where M is a trivalent metal of Group 3b, $X_1$, $X_2$ and $X_3$ are independently selected from the group consisting of:
(a) $NO_2$;
(b) R, wherein R is a saturated or unsaturated hydrocarbon and has 1 to 20 carbon atoms;
(c) $Si(R')_3$, wherein R' is the same or different, and is a saturated or unsaturated hydrocarbon having 1 to 20 carbon atoms or an alkoxy group having 1 to 10 carbon atoms; and (d) 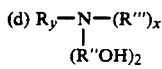

wherein each R'' is independently a hydrocarbon having 1 to 20 carbon atoms, wherein R''' is a hydrocarbon having 1 to 20 carbon atoms or a hydrogen atoms;
wherein R, R', R'' and R''' are independently saturated or unsaturated;
y represents 1 and x and z independently represent 0, 1 or 2 and x+y+z equals 3;

(e) 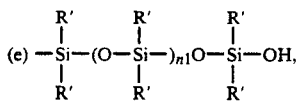

wherein n1 is 1 to 10 and R' has 1 to 20 carbon atoms or is a hydrogen atom;
wherein at most two of the group $X_1$, $X_2$ and $X_3$ of formula I are substituent (a);
wherein the alcohol is HO—(b);
wherein the silanol is HO—(c) or HO—(e); and
wherein the alkanolamine is HO—(d).

41. The process according to claim 36, wherein the Group 3b metal is cerium and the complex is cerous nitrate ammonium nitrate complex, further comprising preparing the cerous nitrate ammonium nitrate complex by reducing ceric ammonium nitrate with anhydrous ammonia.

42. The process according to claim 36, wherein the Group 3b metal is cerium and the complex is cerous nitrate ammonium nitrate complex, further comprising preparing the cerous nitrate ammonium nitrate complex by reducing ceric ammonium nitrate with an alcohol and sufficient ultraviolet irradiation or catalyst to effect the reduction.

43. The process according to claim 37, wherein the Group 3b metal is cerium and the complex is cerous nitrate ammonium nitrate complex, further comprising preparing the cerous nitrate ammonium nitrate complex by reducing ceric ammonium nitrate with anhydrous ammonia.

44. The process according to claim 37, wherein the Group 3b metal is cerium and the complex is cerous nitrate ammonium nitrate complex, further comprising preparing the cerous nitrate ammonium nitrate complex by reducing ceric ammonium nitrate with an alcohol and sufficient ultraviolet irradiation or catalyst to effect the reduction.

45. The process according to claim 38, wherein the Group 3b metal is cerium and the complex is cerous nitrate ammonium nitrate complex, further comprising preparing the cerous nitrate ammonium nitrate complex by reducing ceric ammonium nitrate with anhydrous ammonia.

46. The process according to claim 38, wherein the Group 3b metal is cerium and the complex is cerous nitrate ammonium nitrate complex, further comprising preparing the cerous nitrate ammonium nitrate complex by reducing ceric ammonium nitrate with an alcohol and sufficient ultraviolet irradiation or catalyst to effect the reduction.

47. The process according to claim 39, wherein the Group 3b metal is cerium and the complex is cerous nitrate ammonium nitrate complex, further comprising preparing the cerous nitrate ammonium nitrate complex by reducing ceric ammonium nitrate with anhydrous ammonia.

48. The process according to claim 39, wherein the Group 3b metal is cerium and the complex is cerous nitrate ammonium nitrate complex, further comprising preparing the cerous nitrate ammonium nitrate complex by reducing ceric ammonium nitrate with an alcohol and sufficient ultraviolet irradiation or catalyst to effect the reduction.

49. The process according to claim 40, wherein the Group 3b metal is cerium and the complex is cerous nitrate ammonium nitrate complex, further comprising preparing the cerous nitrate ammonium nitrate complex by reducing ceric ammonium nitrate with anhydrous ammonia.

50. The process according to claim 40, wherein the Group 3b metal is cerium and the complex is cerous nitrate ammonium nitrate complex, further comprising preparing the cerous nitrate ammonium nitrate complex by reducing ceric ammonium nitrate with an alcohol and sufficient ultraviolet irradiation or catalyst to effect the reduction.

51. The process according to claim 1 wherein any two $X_1$, $X_2$ or $X_3$ of the same molecule or a different molecule of formula 1 are represented by a single group selected from (e) where $R=CH_3$ and $q=1$.

52. The process according to claim 51, wherein the Group 3b metal is cerium and the complex is cerous nitrate ammonium nitrate complex, further comprising preparing the cerous nitrate ammonium nitrate complex by reducing ceric ammonium nitrate with anhydrous ammonia.

53. The process according to claim 51, wherein the Group 3b metal is cerium and the complex is cerous nitrate ammonium nitrate complex, further comprising preparing the cerous nitrate ammonium nitrate complex by reducing ceric ammonium nitrate with an alcohol and sufficient ultraviolet irradiation or catalyst to effect the reduction.

* * * * *